United States Patent [19]

Helmlinger et al.

[11] Patent Number: 5,072,019
[45] Date of Patent: Dec. 10, 1991

[54] PROCESS FOR THE MANUFACTURE OF 4-(2-BUTENYLIDENE)-3,5,5-TRIMETHYL-2-CYCLOHEXEN-1-ONE

[75] Inventors: Daniel Helmlinger, Gockhausen; Frank Kienzle, Flüh; Erich Widmer, Müchenstein, all of Switzerland

[73] Assignee: Givaudan Corporation, Clifton, N.J.

[21] Appl. No.: 649,772

[22] Filed: Feb. 1, 1991

Related U.S. Application Data

[62] Division of Ser. No. 399,208, Aug. 28, 1989, Pat. No. 5,015,779.

[30] Foreign Application Priority Data

Aug. 30, 1988 [CH] Switzerland ............ 3216/88
Jun. 22, 1989 [CH] Switzerland ............ 2324/89

[51] Int. Cl.$^5$ ............................. C07C 69/78
[52] U.S. Cl. .................... 560/100; 560/259; 568/378; 558/260; 558/270
[58] Field of Search ............ 568/378; 560/106, 259; 558/260, 270

[56] References Cited

U.S. PATENT DOCUMENTS

| | | | |
|---|---|---|---|
| 2,827,481 | 3/1958 | Isler et al. | 568/378 |
| 3,211,157 | 10/1965 | Rowland | 508/378 |
| 3,217,718 | 11/1965 | Roberts | 568/378 |
| 3,559,656 | 2/1971 | Heckman | 568/378 |
| 3,899,517 | 8/1975 | Mookherjee et al. | 263/348 |
| 4,054,606 | 10/1977 | Nüf | 568/348 |
| 4,072,711 | 2/1978 | Noegeli | 568/838 |
| 4,255,213 | 3/1981 | Wilson et al. | 568/886 |
| 4,405,417 | 9/1983 | Grass et al. | 568/378 |
| 4,753,924 | 6/1988 | Brunke et al. | 512/15 |

FOREIGN PATENT DOCUMENTS

| | | | |
|---|---|---|---|
| 3516931 | 11/1986 | Fed. Rep. of Germany | 568/378 |
| 60-156666 | 8/1985 | Japan | 860/259 |

OTHER PUBLICATIONS

Sefton et al., Chem. Abst., vol. 112, #137419u (1990).
Fujimori, Chem. Abst., vol. 92, #55309n (1980).
Enyell et al., Chem. Abst., vol. 104, #222,183s (1986).
L. Cerveny et al., Parfumerie und Kosmetik, 69 (1988) 9–16.
E. Demole et al., Helv. Chim. Acta. 57 (1974) 2087–9.
B. Trost et al., J. Amer. Chem. Soc., 97 (1975) 4018–25.
S. Torii et al., Bull. Chem. Soc. Japan, 52 (1979) 1233–4.
O. Takazawa et al., Bull. Chem. Soc. Japan, 55 (1982) 1907–11.
Fujimori et al., 7th International Congress of Essential Oils, (1977), FIG. 4.
R. Wilson et al., Tobacco Report (1983) 42.
"Organikum Org. Chem. Grundpraktikum", VEB Deutscher Verlag der Wissen-Schaften, Berlin (1986) 402 et seq.
"Organic Reactions", VIII, J. Wiley, New York-London (1954) 28–35.
H. Mayer et al., Helv. Chim. Acta. 50 (1967) 1606.
C. P. Biandu, Chem. Abst., vol. 96, #217,331 (1982).

*Primary Examiner*—James H. Reamer
*Attorney, Agent, or Firm*—Robert F. Tavares; Linda A. Vag

[57] ABSTRACT

A method for the manufacture of the four geometric isomers of 4-(2-butenyl)idene)-3,5,5-trimethy-2-cyclohexen-1-one is provided. The process comprises pyrolyzing a compound of the formula

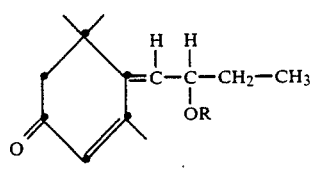

II wherein R represents lower-alkyl-oxycarbonyl, aryl-oxycarbonyl, or, preferably, lower-alkanoyl, benzoyl or substituted benzoyl.

6 Claims, No Drawings

PROCESS FOR THE MANUFACTURE OF 4-(2-BUTENYLIDENE)-3,5,5-TRIMETHYL-2-CYCLOHEXEN-1-ONE

This application is a division of application Ser. No. 07/399,208 filed: Aug. 28, 1989, U.S. Pat. No. 5,015,779 PROCESS FOR THE MANUFACTURE OF 4-(2-BUTENYLIDENE)-3,5,5-TRIMETHYL-2-CYCLOHEXEN-1-ONE.

SUMMARY OF THE INVENTION

The process of this invention provides a novel method for the manufacture of 4-(2-butenylidene)-3,5,5-trimethyl-2-cyclohexen-1-one (I) (megastigmatrienone), a known flavoring component of tobacco. More particularly, the invention provides a process for the manufacture of a mixture of the four possible geometric isomers of megastigmatrienone, as shown below. wherein Ia represents the ZZ-isomer; Ib represents the ZE-isomer; Ic represents EZ-isomer; and Id represents the EE-isomer.

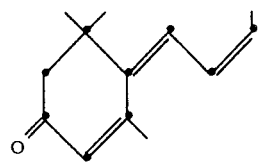
Ia

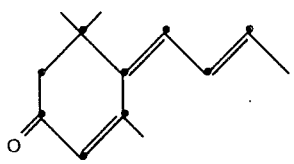
Ib

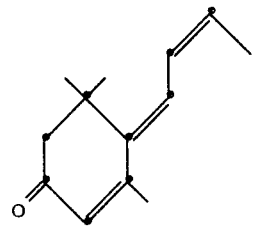
Ic

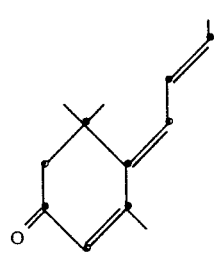
Id

The novel method comprises pyrolyzing a compound of the formula

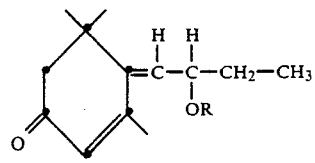
II wherein R represents a lower-alkanoyl group, for example an alkanoyl group containing from one to six carbon atoms; an optionally substituted benzoyl group, for example, one substituted by a lower alkyl group containing from one to six carbon atoms such as a methyl group; a lower alkyl-oxycarbonyl group of the formula

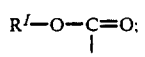

or an aryl-oxycarbonyl group of the formula

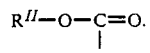

$R^I$ is preferably an alkyl group of one to six carbon atoms such as methyl or ethyl. $R^{II}$ is preferably phenyl or tolyl. Examples of R are acetyl, propionyl, butyroyl, caproyl, benzoyl and toluoyl. Acetyl is a preferred substituent.

The compounds of formula II may exist as a mixture of two possible geometric (Z- and E-) isomers, namely

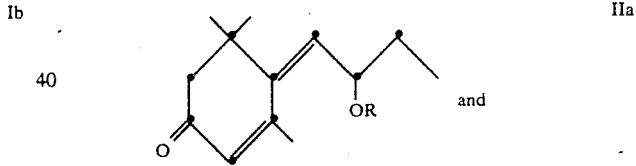
IIa and

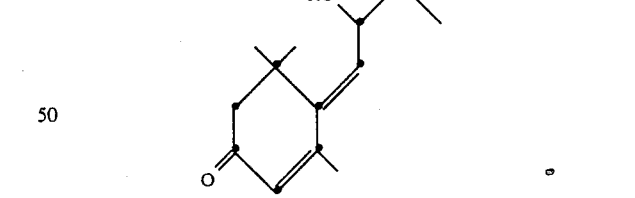
IIb

For purposes of the present invention, it is preferred to use a mixture of the two isomers.

The compounds of formula II are conveniently prepared by esterifying 4-(2-hydroxybutylidene)-3,5,5-trimethyl-2-cyclohexen-1-one (III), preferably as the Z- and E-isomer mixture

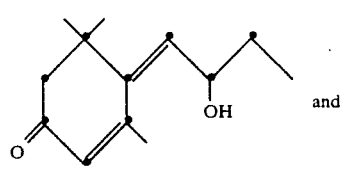
IIIa and

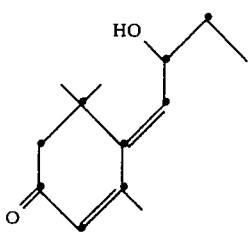

The compound of formula III may be prepared by reacting (2,6,6-trimethyl-4-oxo-2-cyclohexen-1-ylidene)acetaldehyde (IV), preferably as the Z- and E-isomer mixture

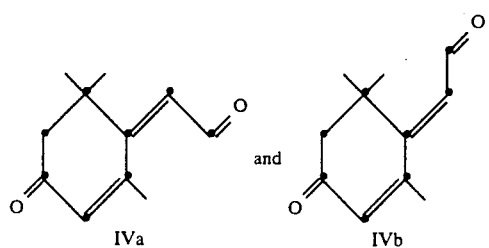

with an organometallic reagent.

The compounds of formulas II and III are novel and are also an object of this invention.

A number of synthetic methods for the manufacture of megastigmatrienone are available from the prior art:
(1) U.S. Pat. No. 3,211,157
(2) U.S. Pat. No. 3,217,718
(3) E. Demole, P. Enggist, Helv. Chim. Acta 57, 2087–2089, (1974)
(4) B. M. Trost, J. L. Stanton, JACS 97, 4018–4025, (1975)
(5) S. Torrii, J. Inokuchi, H. Ogawa, Bull. Chem. Soc. Japan 52, 1233–1234, (1979)
(6) O. Takazawa, H. Tamura, K. Kogami, K. Hayashi, Bull. Chem. Soc. Japan 55, 1907, (1982)
(7) German Offenlegungsschrift 35 16 931.

These syntheses all suffer from disadvantages such as:
a) the use of problematic reagents (2), (7);
b) non-uniform reaction products (3);
c) expensive reagents (4), (5), (6); and
d) difficultly accessible starting materials (1).
None of these disadvantages are associated with the present process.

The present process has the further advantage that the isomer distribution of Ia to Id comes close to the isomer distribution which is found in nature. (See e.g. T. Fujimori, R. Kasuga, H. Kaneko, M. Noguchi, Central Research Institute, The Japan Tobacco and Salt Public Corporation, Yokohama, Japan; Presentation at the 7th International Congress of Essential Oils, Kyoto, Japan, 1977, FIG. 4 "Gas chromatogramm of the neutral volatile fraction of leaves before curing and aging"; see also Tobacco Report, October 1983, 42.)

ILLUSTRATION OF THE PREFERRED EMBODIMENTS

The pyrolysis of compound II is conveniently carried out at temperatures of about 400°–600° C., especially at about 450°–550° C., under an inert gas atmosphere, such as nitrogen or in a noble gas atmosphere. The mixture of isomers of compound I obtained from the pyrolysis may be conveniently purified by standard methods such as distillation.

Compound II may be prepared by the esterification of 4-(2-hydroxybutylidene)-3,5,5-trimethyl-2-cyclohexen-1-one (III). This esterification may be conveniently carried out using customary acylating agents, such as acyl halides, especially the chloride, or acid anhydrides. The use of acid anhydrides is preferred. The acylation is conveniently carried out in the presence of a base, e.g. an organic amine such as pyridine or dimethylamine. An inert solvent, e.g. a hydrocarbon or an ether, such as hexane, cyclohexane, toluene, diethyl ether, etc. may be used but is not necessary. A suitable temperature range is that of about 20° C.–80° C. (See Organikum, Org. Chem. Grundpraktikum VEB Deutscher Verlag der Wissenschaften, Berlin (1986), page 402 et seq.)

The preparation of the hydroxy compound III may be carried out by reacting the ketoaldehyde IV with an appropriate organometallic reagent such that the side-chain at the aldehyde function is lengthened by two carbon atoms. A convenient reagent is accessible by the reaction of $C_2H_5MgX$ with a reagent of the formula $MX_2$, or $C_2H_5MgX$ with $(C_2H_5)_2M$, or is $(C_2H_5)_2M$, wherein M represents zinc or cadmium and X is bromine, chlorine or iodine. The use of $C_2H_5MgX/MX_2$ is preferred, particularly $C_2H_5MgCl/ZnCl_2$.

The reaction may be carried out in a manner analogous to those known in the art. (See for example Organic Reactions VIII, 31; J. Wiley, New York-London (1954) 31.) The halide, $C_2H_5MgX$, in ether, may be added at room temperature, to the halide $MX_2$, followed by addition of an ethereal solution of IV. The working-up is carried out by extracting III with an organic solvent.

The ketoaldehyde IV is known. (See for example H. Mayer, M. Montavon, R. Ruegg, O. Isler. Helv. Chim. Acta 50, Fasc. 6 (1967), page 1606, or U.S. Pat. No. 2,827,481.) An especially suitable isomer mixture of IV for the present synthesis consists of about 25 to 35% of the E-isomer and to about 75 to 65% of the Z-isomer. Such a mixture is readily accessible, for example, from 3,5,5-trimethyl-4-hydroxy-4-ethynylcyclohex-2-en-1-one by rearrangement using catalysts based on silyl-vanadates in a manner known per se. Tris(triphenyl-silyl)-vanadate is preferred. (See L. Cerveny and Vlastimil Ruzicka, Parfümerie und Kosmetik, 69 (1), 9, (1988).)

The isomer distribution of IV is essentially retained in the subsequent steps described above.

ILLUSTRATION OF THE PREFERRED EMBODIMENTS

Example a) Lithium (15 g, 2.2 mol) in small pieces is added within one hour to 900 ml of ammonia at −35° C. Acetylene is conducted through the mixture until the blue color has disappeared and a grey suspension results. Ketoisophorone (150 g, 1 mol) is then added dropwise. The ammonia is evaporated within 12 hours. An orange colored residue remains. Subsequently, 1 liter of ice-/water is added, the mixture is treated while stirring with ether and then with 2N HCl and thereafter made acid with conc. HCl. The phases are separated and the aqueous phase is extracted four times with ether. The ether extracts are washed twice with water and with saturated sodium chloride solution, dried, filtered and concentrated. In this manner there are obtained 166 g of crude 3,5,5-trimethyl-4-hydroxy-4-ethynylcyclohex-2-en-1-one. This crude product is dissolved almost completely in 500 ml of ether and then cooled to −25°. In this manner there are obtained 86.2 g (48%) of crystalline 3,5,5-trimethyl-4-hydroxy-4-ethynylcyclohex-2-en-1-one. The mother liquor is dissolved in 140 ml of isopropyl ether and cooled to 0°. In this manner there are obtained a further 25 g (14%) of crystals of the desired compound.

b) Triphenylsilanol (22 g) and 80 g (0.45 mol) of 3,5,5-trimethyl-4-hydroxy-4-ethynylcyclohex-2-en-1-one and 1.6 g of stearic acid are dissolved in 800 ml of xylene, treated with 1.92 ml of vanadium isopropylate and heated to reflux temperature while stirring. After 3½ hours the reaction mixture is cooled and washed with 5% sodium bicarbonate, whereby an emulsion results. The organic phase is then separated, the emulsion is also separated and extracted with ether. The organic phases are dried over magnesium sulphate and concentrated. The residue (117.9 g) is distilled (oil bath 130°-170°; 0.001 mm Hg). In this manner there are obtained 51.8 g (64.8%) of (2,6,6-trimethyl-4-oxo-2-cyclohexen-1-ylidene)acetaldehyde (Z:E=about 3:1).

c) Ethyl iodide (122.6 g, 0.786 mol) in 100 ml of ether is added dropwise within 40 minutes to 19.1 g (0.786 mol) of magnesium in ether. The mixture is left to react at room temperature for 12 hours while stirring. The reagent formed is added dropwise within 40 minutes to 107.14 g (0.786 mol) of zinc chloride in 400 ml of ether (slight exothermic reaction). The mixture is left to react at reflux temperature for 1½ hours while stirring. Then, 100 g (0.562 mol) of (2,6,6-trimethyl-4-oxo-2-cyclohexen-1-ylidene)acetaldehyde dissolved in 400 ml of ether are added at room temperature within 30 minutes while stirring. After half of the addition a viscous paste forms, but this again dissolves. The mixture is subsequently stirred at reflux for 4 hours and at room temperature for 48 hours. The reaction mixture is poured on to ice and extracted with ether. The organic solution is washed neutral three times with 300 ml of water each time and then with 300 ml of saturated sodium chloride solution. The organic phase is dried over magnesium sulphate and evaporated. There are obtained 104 g of a mixture of (Z)-4-(2-hydroxybutylidene)-3,5,5-trimethyl-2-cyclohexen-1-one and (E)-4-(2-hydroxybutylidene)-3,5,5-trimethyl-2-cyclohexen-1-one which is reacted immediately.

d) Acetic anhydride (54.9 g, 0.54 mol) is added at room temperature to 104 g (0.5 mol) of the above mixture in 500 ml of pyridine. After stirring at room temperature for 18 hours the pyridine is distilled off. The residue is dissolved in ether and washed twice with 2N HCl, with saturated sodium bicarbonate solution, with water and with saturated sodium chloride solution and dried over magnesium sulphate. Crude product (107.15 g) is distilled. (B.p. @ 0.001 Torr, 117°-140°, heating bath 136°-185°). In this manner there are obtained 86 g of 4-(2-acetoxybutylidene)-3,5,5-trimethyl-2-cyclohexen-1-one [Z/E=73/26] corresponding to 61.4% of theory based on (2,6,6-trimethyl-4-oxo-2-cyclohexen-1-ylidene)acetaldehyde.

e) The pyrolysis apparatus used in this example consists of:
  a) Pre-heating tube: Pyrex, 30 cm, 2.5 cm φ, Raschig rings 7×7 mm, heating mantle.
  b) Main heating tube: Quartz, 32 cm, 2.5 cm φ, Raschig rings 6×6 cm, muffle furnace.

4-(2-Acetoxybutylidene)-3,5,5-trimethyl-2-cyclohexen-1-one (90 g, 0.36 mol) is pyrolyzed (pre-heating tube 190°, main heating tube 500°) within 6 hours under a nitrogen stream of 6 ml/minute and under a water-jet vacuum (11 mm Hg) with a dropwise addition rate of 3-5 drops per minute. The reaction product is collected in a flask which is cooled to −70° C. Two head fractions are subsequently distilled over a 10 cm Widmer column and have the following characteristics:

Fraction 1: Bath 128°; 0.001 Torr; b.p. 40°-98°; 4.9 g.
Fraction 2: Bath 128°; 0.001 Torr; b.p. 98°; 5.1 g.

The residue is subjected to short-path distillation at 120°/0.1 Torr. In this manner there are obtained 55.1 g (80%) of 4-(2-butenylidene)-3,5,5-trimethyl-2-cyclohexen-1-one. Isomer ratio: 19,48% ZZ, 41,30% ZE, 12,34% EZ, 26,86% EE.

We claim:

1. A compound of the formula

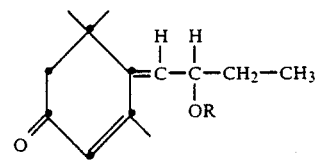

wherein R represents hydrogen, lower-alkanoyl, benzoyl, substituted benzoyl, lower-alkyl-oxycarbonyl or aryl-oxycarbonyl.

2. A compound according to claim 1 wherein R represents hydrogen, lower alkanoyl, benzoyl or substituted benzoyl.

3. A compound according to claims 1 or 2 which is a mixture of the E- and the Z-geometric isomers.

4. A compound according to claim 3 wherein the ratio of the E- to the Z-isomer is about 25-35:65-75.

5. A compound according to claim 4 wherein the lower alkanoyl contains an alkyl group having from one to six carbon atoms and the substituted benzoyl is substituted with an alkyl group having from one to six carbon atoms.

6. A compound according to claim 5 wherein R represents hydrogen, acetyl, propionyl, butyroyl, caproyl, benzoyl or toluoyl.

* * * * *